(12) United States Patent
Reinhardt et al.

(10) Patent No.: US 7,161,266 B2
(45) Date of Patent: Jan. 9, 2007

(54) TRI-AXIAL HANDLING APPARATUS

(75) Inventors: Thomas Reinhardt, Ettlingen (DE); Manfred Berndt, Karlsbad (DE)

(73) Assignee: Agilent Technologies, Inc., Palo Alto, CA (US)

( * ) Notice: Subject to any disclaimer, the term of this patent is extended or adjusted under 35 U.S.C. 154(b) by 678 days.

(21) Appl. No.: 10/247,178

(22) Filed: Sep. 19, 2002

(65) Prior Publication Data

US 2003/0113232 A1   Jun. 19, 2003

(30) Foreign Application Priority Data

Dec. 14, 2001   (EP)   ................... 01129773

(51) Int. Cl.
*H02K 41/00*   (2006.01)
(52) U.S. Cl. .................... 310/12; 310/13; 422/99; 422/100; 422/101; 436/180
(58) Field of Classification Search .......... 422/99–101; 436/180; 310/12–13
See application file for complete search history.

(56) References Cited

U.S. PATENT DOCUMENTS 5,275,951 A * 1/1994 Chow et al. .................. 436/50

6,313,551 B1 * 11/2001 Hazelton ..................... 310/12

FOREIGN PATENT DOCUMENTS

| EP | 0 868 962 | 10/1998 |
|---|---|---|
| WO | WO 01/82013 | 11/2001 |

OTHER PUBLICATIONS

De Gussem, J., Examiner. European Search Report Application No. EP 01 12 9773 dated Aug. 22, 2002.

* cited by examiner

*Primary Examiner*—Jill Warden
*Assistant Examiner*—Jyoti Nagpaul

(57) ABSTRACT

A tri-axial handling apparatus, in particular for fluid analysis devices, for example for micro-fluid analysis. The handling apparatus comprises at least three axle bodies, each exhibiting a guide component and a carrier component, which by means of a drive is translationally movable on the guide component in the direction of an axis of movement. A guide component of a first axial body is secured to the carrier component of a second axial body, whose guide component is secured to the carrier component of a third axial body. Preferably, each drive for the respective carrier component is a linear motor, which is secured to the respective axle body.

13 Claims, 8 Drawing Sheets

TRI-AXIAL HANDLING APPARATUS

FIELD OF THE INVENTION

The invention concerns a tri-axial handling apparatus, in particular for fluid analysis devices, for example for micro-fluid analysis, in particular bio-analysis, for example DNA, RNA or protein analysis, for the analysis, addition and/or removal of fluids to or from small recesses of a micro-titer plate or fluid chip, with at least three axle bodies, each exhibiting a guide component and a carrier component, which by means of a drive is translationally movable on the guide component in the direction of an axis of movement, wherein at least three axes of movement respectively form a space angle to each other and are preferably each positioned vertically to each other, wherein a guide component of a first axle body is secured to the carrier component of a second axle body, whose guide component is secured to the carrier component of a third axle body, wherein the carrier component of the first axle body forms a handling carrier designed to enable a handling operation within a manipulation area determined by the axes of movement.

DISCUSSION OF THE BACKGROUND ART

Such a tri-axial or 3D handling apparatus is generally known for a fluid analysis apparatus. In this case, fluid analysis uses what are referred to as micro-titer plates, which exhibit a number of small recesses, referred to as "wells" arranged in a matrix, which accommodate the fluid to be analysed. The number of wells is typically 96 or 384, up to 1536. Fluid is added to or removed from the wells or analysed by means of what is referred to as a pipette head. This is secured to the handling carrier of a tri-axial apparatus of the aforementioned kind and can be moved in three axes of movement positioned vertically to each other by means of a horizontal x-axis, a horizontal y-axis arranged offset to it by 90° and a vertical z-axis in turn arranged offset to both the x-axis and the y-axis by 90° within a manipulation area determined by these axes of movement. The vertical z-axis thus forms the last of the three axes of movement to be moved.

For adding or removing fluid to or from the wells or for analysing the fluid, the micro-titer plate remains stationary, whilst the pipette head is moved with the aid of the 3D handling apparatus. Consequently, to approach a particular well, the pipette head must be moved downwards in the direction of the z-axis, and after adding, removing or analysing fluid, moved back upwards in the direction of the z-axis. These handling operations are consequently carried out when the pipette head is fully extended in a downwards direction. This results in a comparatively large degree of play, which means that appropriate limits are set to ensure precision with each respective handling operation.

A series of analyses must be conducted at temperatures that have been reduced to below ambient. For this purpose, the entire analysis apparatus currently has to be cooled and operated in a cooling chamber. This is space-consuming and expensive and both handling and accessibility are bad.

The currently known tri-axial handing apparatus for fluid analysis devices have the further disadvantage that in terms of the respective axle body, the potential travel path of the corresponding carrier component is small compared to the corresponding axle length. Thus, current handling apparatus and the analysis devices they accommodate, given a determined travel path or manipulation area, which must be achieved, must be designed to have a comparable high volume. Consequently, the previously known apparatus or devices are relatively space-consuming. This limits their usability and application as laboratory devices accordingly.

Each of the respective carrier components can be moved, with the aid of a servo-motor with belt drives or a step motor with cam plates, in the direction of the respective axes of movement. In order to be able to achieve any desired position with the pipette head within the manipulation area, the drives can be controlled independently of each other. The previously used drives however have the disadvantage of being comparatively expensive, requiring a comparatively large amount of space or construction area and in terms of their movement dynamics, useful life and achievable level of precision, fail to satisfy the requirements placed upon laboratory apparatus or micro-analysis devices.

Finally, use of the previously known drives for the carrier components requires additionally provided path measuring devices to be mounted on each axle body. This is also expensive and these path-measuring devices require additional space. Furthermore, the measuring accuracy in respect of each position of the carrier component is limited accordingly, as determined by the path measuring devices to be provided separately, in addition to the drives.

SUMMARY OF THE INVENTION

The object of the invention is therefore to create a tri-axial handling apparatus for which the components enabling the handling operations use as little space as possible, wherein a particularly compact and simple construction with low weight, reliable long-term operation and favourable guide and positioning conditions is facilitated.

This task is solved by a tri-axial handling apparatus, wherein each drive for the respective carrier component is a linear motor, which is secured to the corresponding axle body.

Use of linear motors for the respective drive of the carrier components can generate the linear lifting movement directly, without mechanical gears, belts, levers or similar, which allows mechanical play and wearing to be minimised. This also allows extreme dynamic movement processes to be realised in a simple manner, without additional components. Such linear motors can be produced as a comparatively small-volume and short structural shape, which allows optimum use of the travel path. The linear motors can also be arranged so as to avoid components projecting beyond the axle bodies, which allows optimum use of the construction area. Finally, linear motors help to achieve favourable guide and drive conditions, which increases useful life in this respect. Furthermore, linear motors allow the simple integration of a path measuring system into the drive, so that the measuring accuracy and therefore the positioning accuracy for each carrier component can be improved.

The aforementioned effects can be further improved if the linear motor comprises a stator and a slider which is movable relative to it, wherein the stator and the slider are electronically contactless connected. In accordance with a particularly preferred advanced design, the linear motor is formed as an electro-magnetic direct linear motor, in particular as a permanently excited, two-phase synchronous motor. With this linear motor, the linear movement is therefore generated directly by means of electro-magnetic forces. In this case, it is beneficial for the stator to be formed as a magnetic rod, which is permanently secured to the guide component and for the slider to be formed as a coil component, which is permanently connected to the movable carrier component. The aforementioned measures enable favourable options to be created for an integrated sliding bearing arrangement and an integrated position recording using magnetic field sensors and an integrated temperature monitoring to be realised. The permanent magnets of the electro-magnetic direct linear motors therefore have a dual function, for both the commutation and also with position detection, for example with the aid of the aforementioned magnetic field or hall sensors.

The aforementioned task is also solved in accordance with an alternative concept solution or in accordance with a particularly beneficial advanced design of the invention, with a tri-axial handling apparatus, in that the carrier component of the first axle body can be moved on its guide component in direction of a horizontal axis of movement, that the carrier component of the second axle body can be moved on its carrier component in the direction of a vertical axis of movement and that the carrier component of the third axle body can be moved on its guide component in the direction of horizontal axis of movement.

This solution is therefore based on the fact that unlike the prior-art principle, it is not the axis of movement that is assigned directly to the handling carrier, which is formed as a vertical axis of movement rather that the last axis of movement to be moved or the last carrier component movable in the direction of the respective axis of movement, forms a horizontal axis of movement at the free end of the handling apparatus or is movable on a horizontal axis of movement. At the same time, the vertical axis of movement is arranged between two of the horizontal axes of movement, relative to either the action or arrangement.

Suitably, at least one carrier component and/or one guide component is formed with a C-shaped or U-shaped profile component, whose profile limbs delimit a receiving space open to the outside, wherein a carrier component can be moved at least partially into the receiving space of its guide component, an adjacent guide component and/or an adjacent carrier component. Through the reciprocal penetration and/or reciprocal interleaving of the stated elements, optimum use can be made of the construction space, assuming low weight.

It is also advantageous for the guide component of the third axle body, which is preferably secured to the device, to be formed with a profile extending in the direction of the associated axis of movement, said profile comprising a basic profile, from which two parallel edge limbs each extend in a direction running parallel to the axis of movement, wherein the guide component of the second axle body is secured to the basic profile of the guide component of the third axle body and extends at least partially between the edge limbs, yet offset from them in such a way that the carrier component guided on the second guide component can be moved at least partially within the C-shaped or U-shaped profile of the guide component of the third axle body.

It is also advantageous if the carrier component guided on the third guide component is at least partially received and movable within the C-shaped or U-shaped profile of the guide component of the third axle body.

In accordance with one advantageous further development, the or each carrier component is embodied as a carriage with at least two opposing running rollers provided with guide slots along their perimeter and open to the outside, which are guidingly mounted on appropriately designed guide rails of the respective guide component. These parallel guide rails can be mounted at the greatest possible distance to the respective guide parts, whereby the guides exhibit the maximum degree of rigidity. Furthermore, the measures described above enable particularly favourable guiding and positioning conditions with extremely low bearing clearance and a long-term reliable function to be achieved.

It is particularly advantageous if the guide rails are embodied as shafts preferably made of steel and secured in the receiving grooves of the guide component. The shafts, preferably exhibiting a circular section are cost-effective and simple to produce, for example by gluing or pinching into the receiving grooves. This serves to further improve the bearing, guiding and strength conditions.

In accordance with a particularly advantageous further development, each guide component exhibits an axial length and a travel path is assigned to each carrier component guided on this guide component, wherein for each axle body the ratio of travel path to axial length is greater than or equal to 0.3, in particular greater than or equal to 0.5. If each individual axis is optimised in this way, a maximum travel path for each axis of movement can be achieved with minimum construction area.

Particularly stable guiding conditions and precise positioning conditions can be achieved by the guide components being embodied with extruded or drawn aluminium profiles.

It is also advantageous if the or each linear motor is arranged between the at least two opposing rollers and the corresponding guide rails. This enables the linear motor to distribute its force in an optimum manner, no tilting occurs and accordingly, no additional force is exerted by the drive onto the bearings, which increases durability. These measures enable the advantages of a permanently excited electro-magnetic direct linear motor to be exploited in such a way that the permanent magnets can be used in combination with a suitable sensor, in particular a magnetic field or hall sensor, to aid path measurement. This enables the path measurement system to measure precisely at the location of the carrier component or the carriage. In this way, maximum positioning accuracy is achieved.

In accordance with one advantageous further development, the invention concerns a Fluid analysis device, for example for micro-fluid analysis, comprising a tri-axial handling apparatus, characterized in that a device for accommodation of fluids to be analyzed, in particular a micro-titer plate or a well plate, can be moved by the handling apparatus in the direction of an analyzing module, in particular a measuring module, pipette module or pipette head respectively and preferably in the direction of a vertical axis of movement by means of the handling carrier.

The aforementioned measures contribute both individually and in any combination, to a tri-axial handling apparatus, for which the components enabling the handling operations require the minimum amount of construction area, and wherein a particularly compact and simple construction with low weight, long-term reliable operation and also favourable guiding and positioning conditions is possible.

BRIEF DESCRIPTION OF THE DRAWINGS

Further features, advantages and principal points of the invention appear in the description which follows, in which a preferred design example is described in more detail with the aid of the Figures.

It shows.

DETAILED DESCRIPTION OF THE PREFERRED EMBODIMENT

Figure 1:
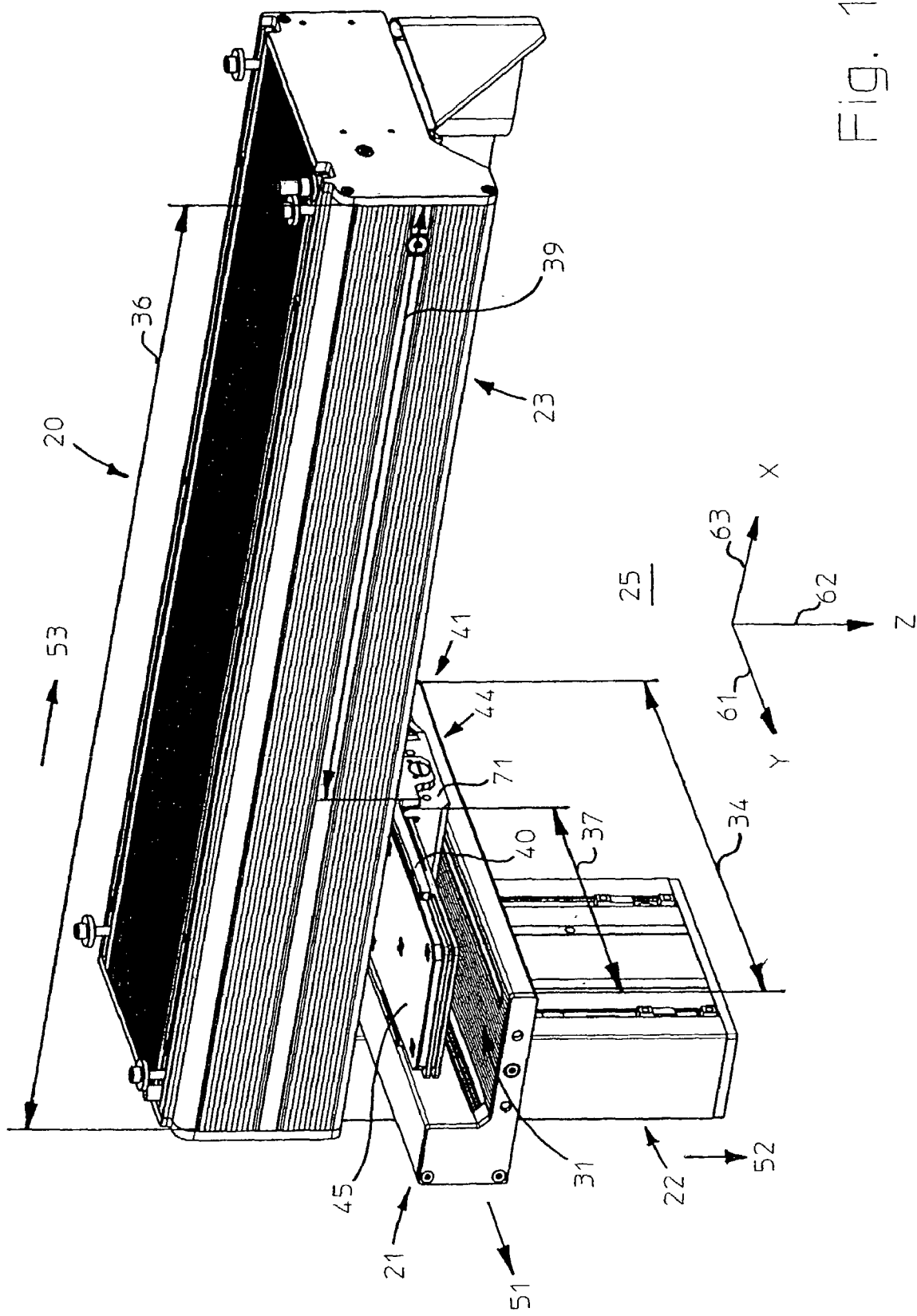
FIG. 1: a three-dimensional view of the handling apparatus of a fluid analysis device exhibiting a gripping and holding device secured to the handling carrier and integral micro-titer plate.
Figure 2:
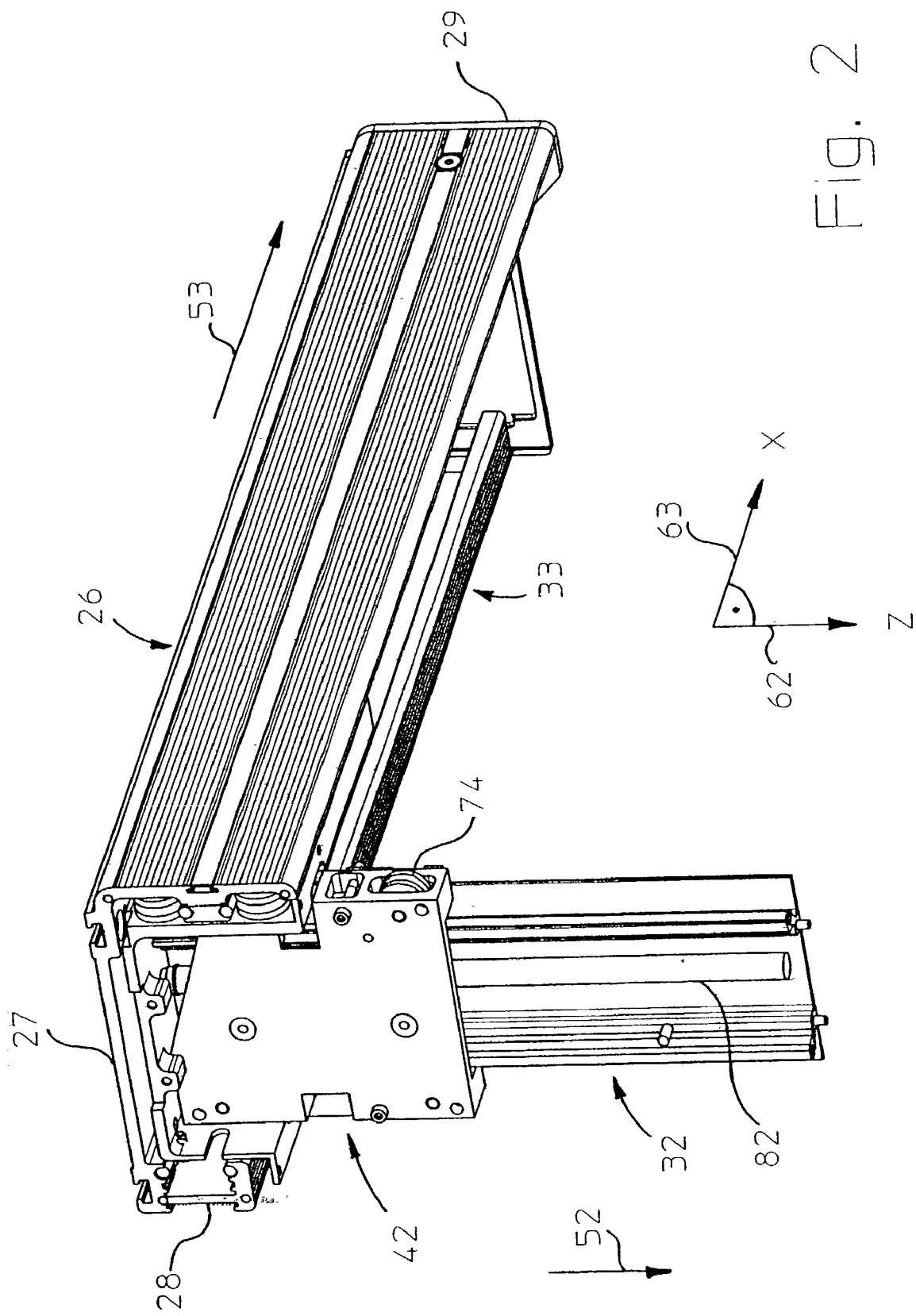
FIG. 2: a three-dimensional view of the third axle body that is assigned a first horizontal axis of movement, with an integral carrier component embodied as a carriage and the guide component of the second axle body embodied as a guide rail secured to it, with the carrier component also embodied as a carriage and guided on this guide component, wherein the second axle body is assigned a vertical axis of movement.

FIG. 1 shows the tri-axial handling device 20 of a fluid analysis device, for which no further details are given. This can be used for micro-fluid analysis, in particular bio-analysis, for example DNA, RNA or protein analysis. The tri-axial handling device 20 serves for an analysis, addition and/or removal of fluids. The transport object to be moved by the tri-axial handling device 20 is typically a micro titer plate 45. This exhibits typically external dimensions of 127.8 mm×85.6 mm. The micro-titer plate 45 comprises a number of wells 46 arranged in a matrix, to which fluid is added or from which fluid is removed and/or in which the fluid can be analysed.

The tri-axial handling device 20 comprises a first axle body 21, also described as a y-axis, a second axle body 22, also described as a z-axis and a third axle body 23, also described as an x-axis. As essential elements, each axle body 21, 22, 23 has a guide component 31, 32, 33, a carrier component 41, 42, 43 guided on it and also a drive 24 for the respective carrier component 41, 42, 43. Each guide component 31, 32, 33 is embodied with an elongated drawn aluminium profile, in such a way as to achieve high inherent rigidity. Each guide component 31, 32, 33 also comprises at least two guide rails 76 arranged offset, parallel and in a common even plane. These are embodied as shafts 78 from steel, which in this case exhibit a circular section. Each shaft 78 is embodied as a straight rod and is secured in a receiving groove 77 of the corresponding guide component 31, 32, 33. This exhibits an internal cross-section formed to suit the external cross-section of the shaft. In the design example, the shafts 78 are glued into the receiving grooves 77. Each guide component 31, 32, 33 together with its guide rails 76 defines a straight axis of movement 51, 52, 53 appropriate to the longitudinal extension of the guide rails 76.

The axial bodies 21, 22, 23 and their guide components 31, 32, 33 are arranged such that their axes of movement 51, 52, 53 respectively form a space angle to each other and, more specifically, in this case, are positioned vertically to each other. This creates an arrangement such that the axes of movement 51, 52, 53 are arranged like a system of co-ordinates and consequently extend in the y-direction 61, z-direction 62 and x-direction 63.

The tri-axial handling device 20 is characterised in that the guide component 31 of the first axle body 21 is secured to the carrier component 41 of the second axial component 22, whose guide component 32 is secured to the carrier component 43 of the third axle body 23. The carrier component 41 of the first axle body forms a handling carrier 44 designed to enable a handling operation within a manipulation area 25 determined by the axes of movement 51, 52, 53.

The third axle body 23, also described as the x-axis, is formed with a U-profile 26, which embodies the guide component 33. The U-profile 26 consists essentially of a basic profile 27, passing over the longitudinal edges in two parallel edge limbs 28, 29, which elevate in the same direction over the basic profile 27.

Figure 4:
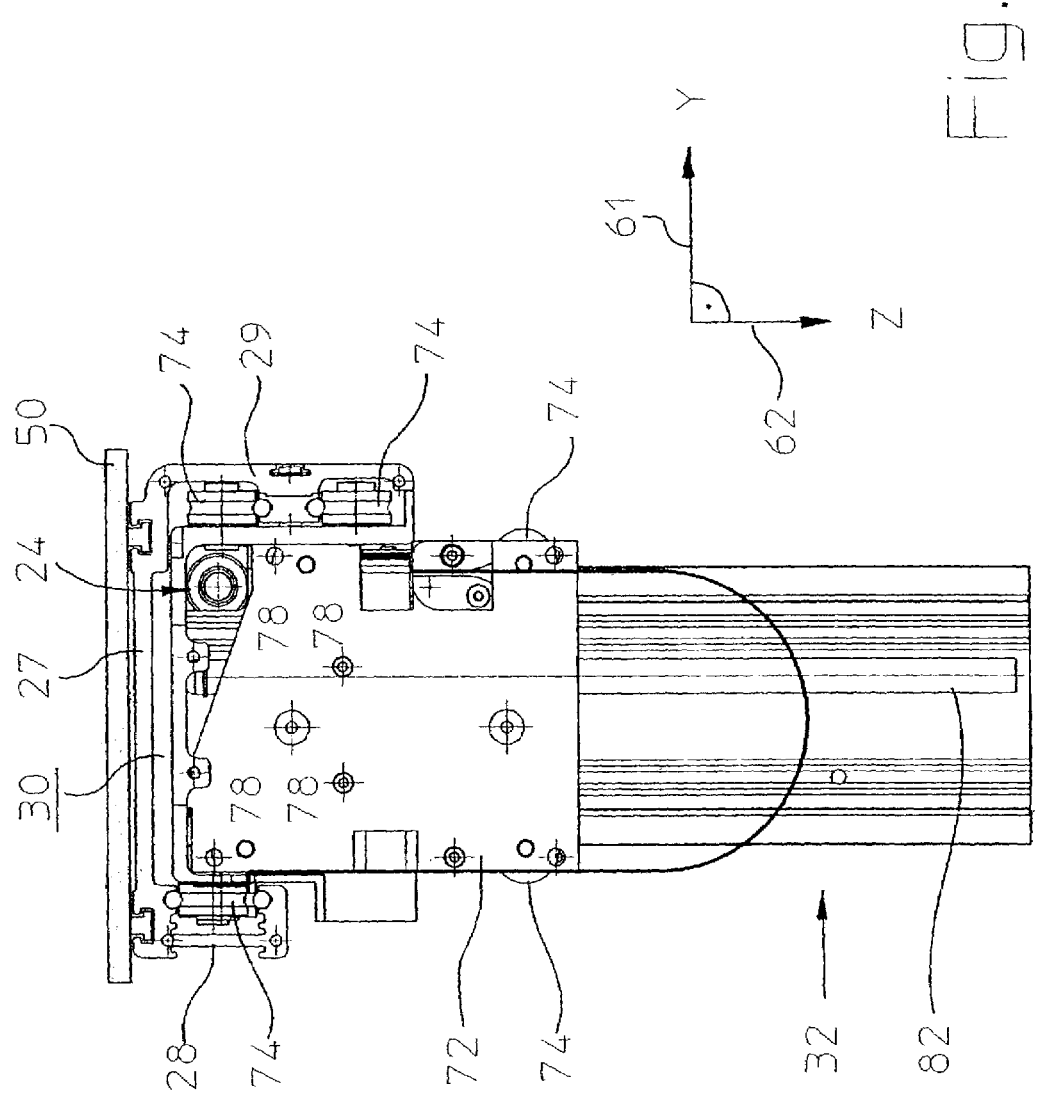
FIG. 4: a side view of the profile components in accordance with FIG. 1.

As shown in particular by the cross-sectional illustration in accordance with FIG. 4, the basic profile 27 exhibits grooves which have a T-shaped cross-section and extending in the x-direction 63 open to the outside, so that the third axle body 23 can be pushed onto the appropriately designed fixing limb of a fixing profile 50 forming a reference plane. The fixing profile 50 is permanently connected to a housing of the micro-analysis device and for which no further details are given. In the installed condition, the entire tri-axial handling apparatus 20 hangs on the underside of the fixing profile 50.

Figure 3:
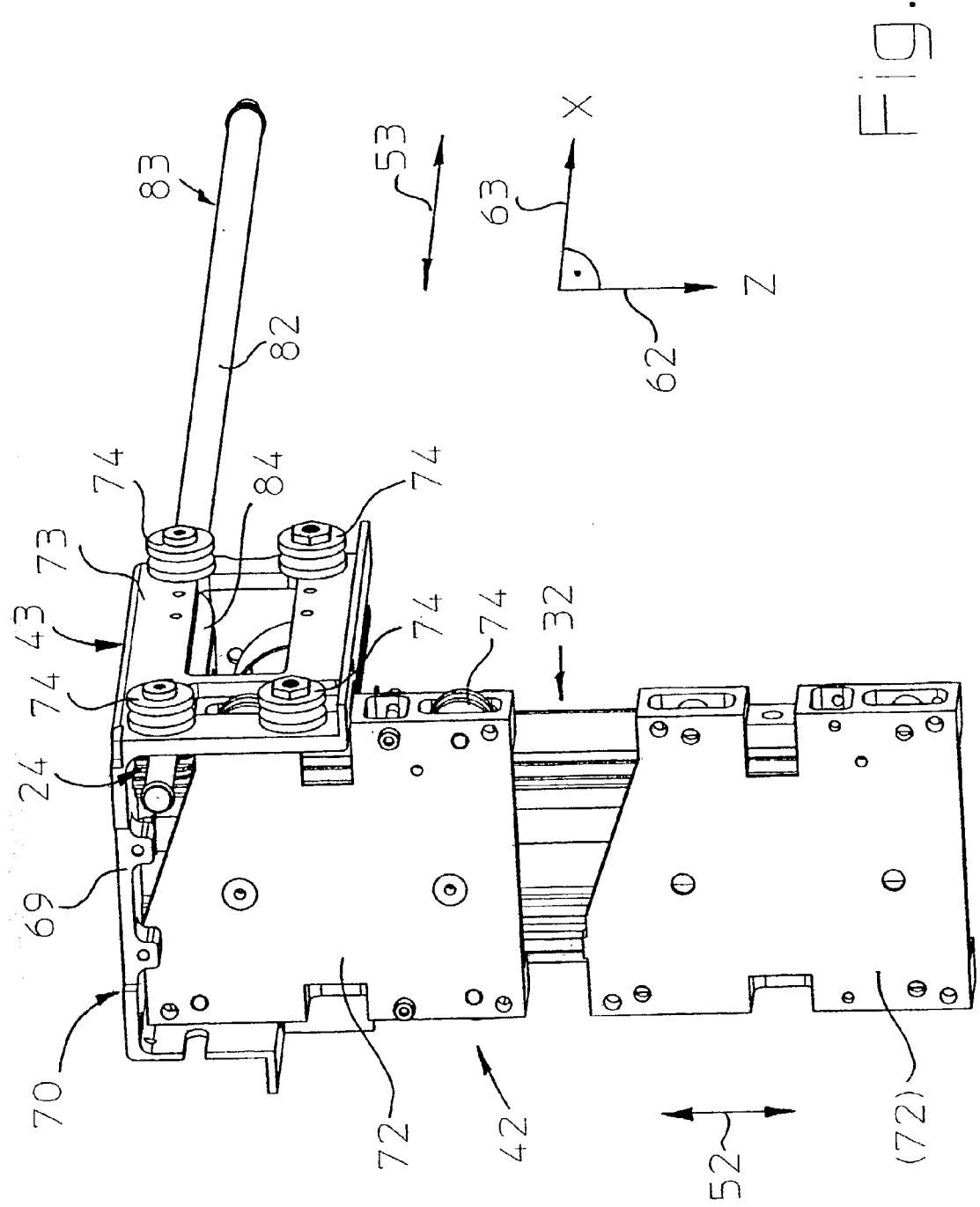
FIG. 3: a three-dimensional view corresponding to FIG. 2, from which the guide component of the third axle body embodied with a U-shaped profile is omitted to show further structural details.

Each edge limb 28, 29 is fitted inwards, i.e. towards the receiving space 30 of the third axle body 23, each with two parallel shafts extending in the x-direction 63. These are arranged in a common, even plane, wherein this plane contains both the axis of movement 53 running in the x-direction 63 and the axis of movement 52 running in the z-direction 62. As FIG. 4 shows, the shafts 78 assigned to the longer, right-hand edge limb 29 are arranged in such a way that opposing rollers 74 of the carriage 73 forming the carrier component 43 are guidingly mounted on these shafts. In contrast, the two shafts 78 assigned to the shorter, left-hand edge limb 28 are arranged offset to each other to leave a receiving space, are arranged in such a way that a roller 74 of the carriage 73 is received, guided and mounted. As shown particularly in FIG. 3, on the edge limb 29 are provided two pairs of two rollers 74, which are arranged offset to each other in the x-direction 63 and which are rotationally movably connected to the carriage 73. In contrast, the shorter edge limb 28 exhibits two rollers 74 arranged offset in an x-direction 63, which are also rotationally movably connected to the carriage 73.

The carriage 73 of the third axle body 23 is also embodied with a U-profile 70 extending in an x-direction 63 and in this direction open to outside. In this arrangement, the pair of rollers of running rollers 74 assigned to the longer edge limb 29 of the guide component 33 are arranged on a longer edge limb of the U-profile 70 of the carriage 73, whilst the running rollers 74 assigned to the shorter edge limb 28 of the guide component 73 are movably mounted and secured on a correspondingly shorter edge limb of the U-profile 70 of the carriage 73. The edge limbs of the carriage 73 are elevated in the same direction on the longitudinal edges of a basic profile 69 and are formed parallel to each other. As FIG. 3 also shows, the guide component 32 of the second axle body 22 extending in the z-direction, i.e. vertically downwards, is secured to the basic profile 69 of the carriage 73 embodied as a carrier component 43 of the third axle body 23, so that when the carriage 73 moves in an x-direction 63, the guide component 32 of the second axle body 22 also moves in an x-direction. The second axle body 22 formed as the z-axis comprises, in addition to the guide component 32, the carriage 72 embodied as a carrier component 42, which is guidingly mounted via the running rollers 74, to the guide rails 76 of the guide component 32, arranged in parallel and offset against each other. The cross-section of the guide component 32 also embodied with a drawn aluminium profile can be seen in FIG. 6. The guide rails 76 formed with shafts 78 are secured to profile limbs of the guide component 22 also formed as a U-profile in such a way that their free roller surfaces point in an opposite direction. The carriage 72 is fitted with a total of four running rollers 74, wherein each shaft 78 is assigned two of the running rollers 74, which are each arranged in a z-direction 62 offset against each other.

To the carriage 72 embodied as a carrier component 42 is secured the guide component 31 of the axle body extending in a y-direction, so that when the carriage 72 moves in a z-direction 62, the first axle body 21 is simultaneously moved in a z-direction 62. As FIG. 1 shows, a carrier component 41 also embodied as a carriage 71 is secured to the guide component 31 of the first axle body 21 so as to be movable in the y-direction. The carrier component 41 embodies the handling carrier 44, to which is secured the gripping and holding device 40 for the micro-titer plate 45.

Accordingly, the tri-axial handling device 20 enables a movement and/or a handling operation of the carrier component 41 of the first axle body within a manipulation area 25 determined by the axes of movement 51, 52, 53.

Each guide component 31, 32, 33 exhibits a certain axis length 34, 35, 36, which corresponds to a maximum guide path corresponding to the length of the guide rails 76. In line with the dimensions of the respective carriage 71, 72, 73 in its corresponding direction of movement, i.e. in y-direction 61, z-direction 62 and x-direction 63, the axle length 34, 35, 36 gives rise to the corresponding maximum travel path 37, 38, 39 for each carriage 71, 72, 73. In the design example, the travel path 37 of the y-axis in a y-direction 61 is 179 mm, whilst the axis length 34 of the guide component 31 is 296 mm. Arithmetically dividing the travel path by the axis length derives the travel path section, which in this case is 61%. In the design example, the travel path 38 of the carriage 72 in the z-direction measures 160 mm, whilst the axle length 35 of the guide component 32 of the z-axis, i.e. in the z-direction 62, measures 310 mm. This gives rise to a travel path section of 0.52 or 52%. In the design example the travel path 39 of the carriage 73 on the x-axis, i.e. in the x-direction 63, measures 435 mm, whilst the axis length 36 of the guide component 33 of the third axle body, i.e. the x-axis, in the x-direction 63, measures 626 mm. From this a travel path section in the x-direction of 0.7 or 70% can be calculated. This indicates optimum use of the available construction space and indicates, given a minimum manipulation area 25 determined by the dimensions of the microtiter plate 45, minimum external dimensions of the tri-axial handling apparatus 20 and/or the micro-fluid analysis device containing it.

Figure 7:
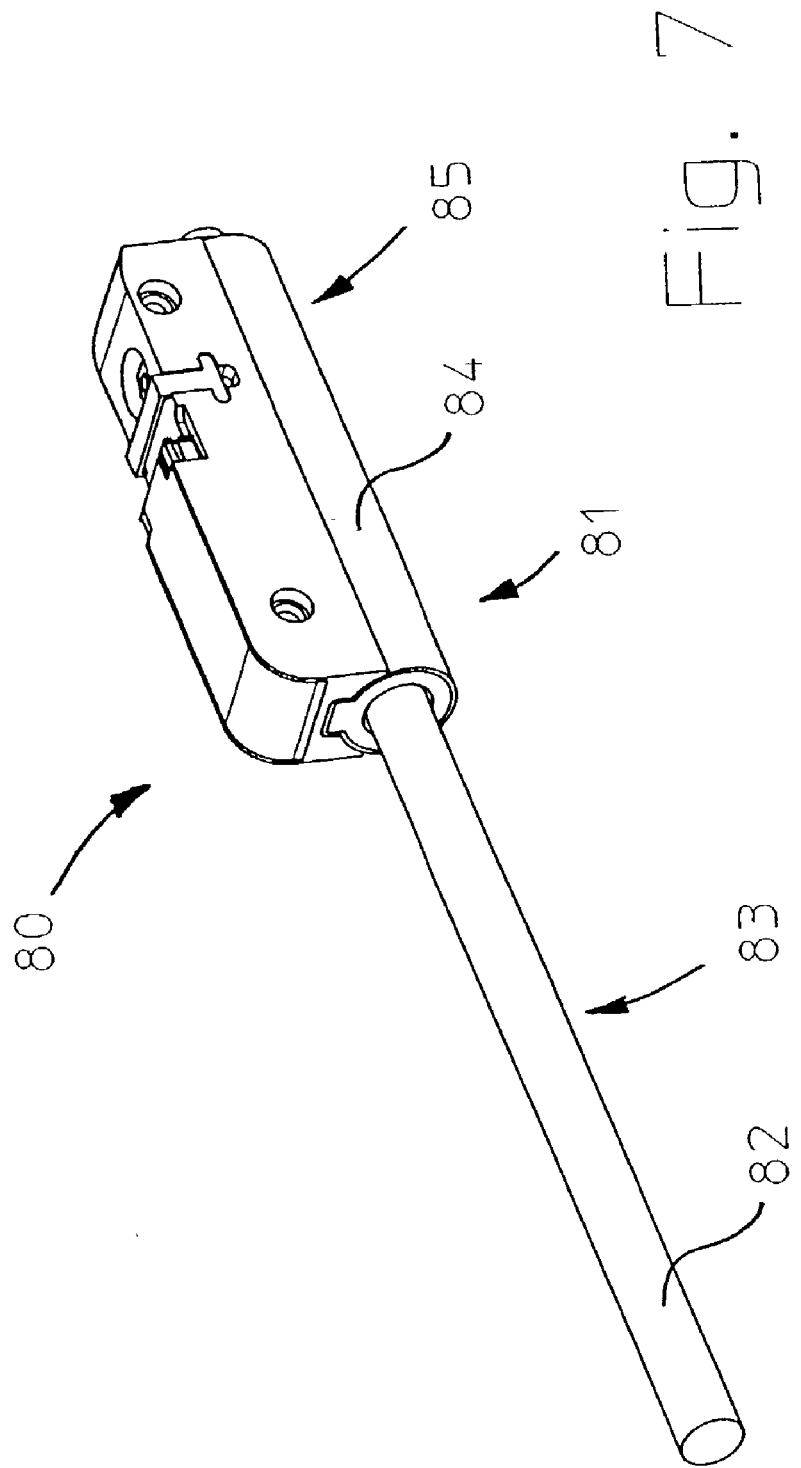
FIG. 7: a three-dimensional view of one of the linear motors.
Figure 8:
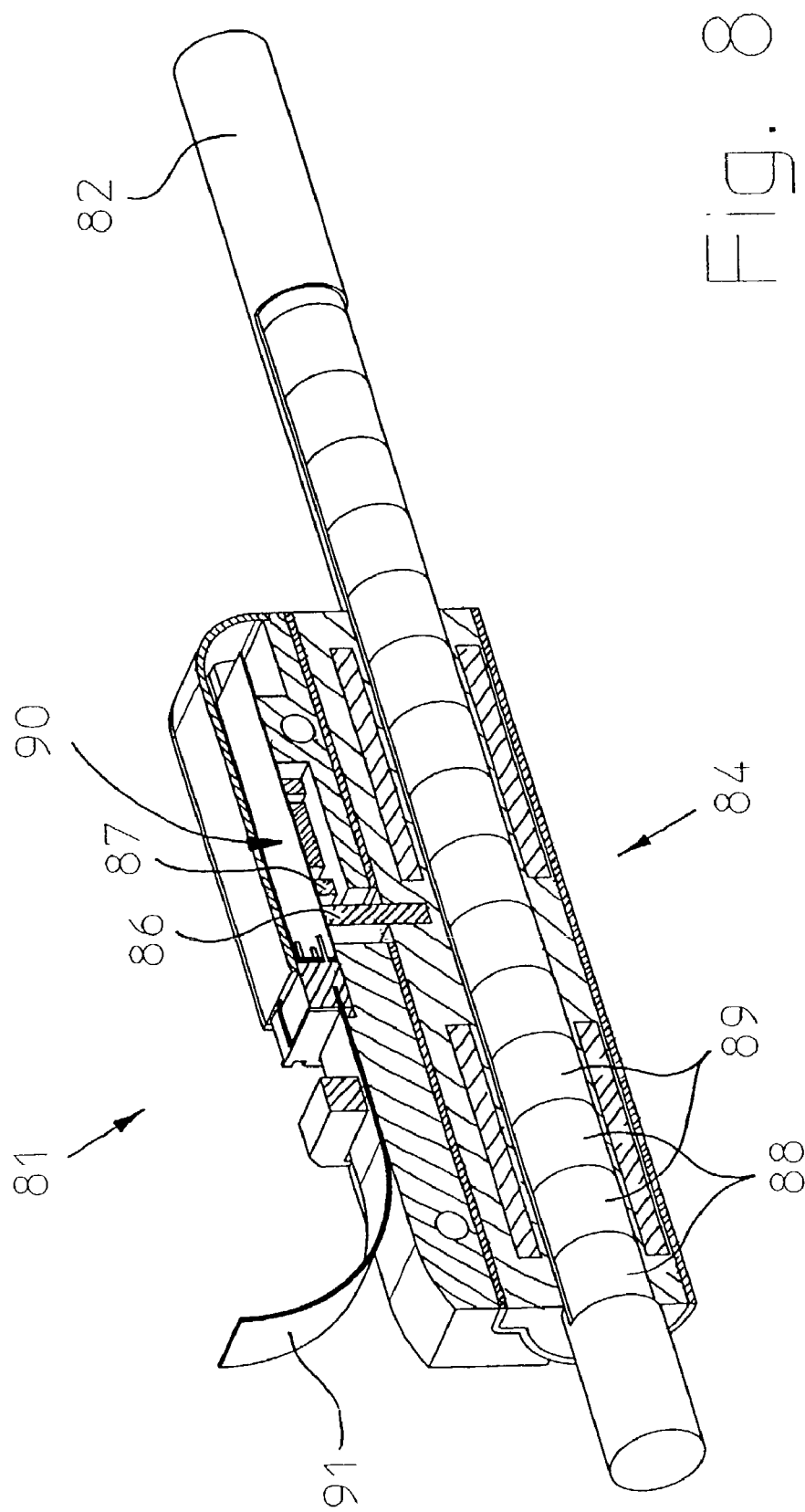
FIG. 8: a schematic cross-section through the linear motor in accordance with FIG. 7.

With the aid of a separate drive secured to each axle body 21, 22, 23, each carriage 71, 72, 73 of the axial bodies 21, 22, 23 can be moved in the direction of the corresponding axes of movement 51, 52, 53, i.e. in a y-direction 61, z-direction 62 and x-direction 63. Each of these drives 24 is a linear motor 80, which in the design example, are embodied as permanently excited, two-phase synchronous, direct linear motors 81. As shown in particular by FIGS. 7 and 8, each direct linear motor 81 consists of a stator 83 and a slider 85. The design example shows the stator 83 embodied as a magnetic rod 82, whilst the slider 85 is embodied as a coil component 84. The magnetic rod 82 is guided over a sliding bearing arranged inside the coil component 84, with extremely low play. As shown by FIG. 8, the coil component 84 comprises stator windings arranged in two phases. The magnetic rod 82 is embodied with the permanent magnets 88 and 89, which are arranged in consecutive alternating polarity inside the magnetic rod 82. In this case, for example, the permanent magnets 88 are arranged in a northerly direction, whilst the permanent magnets 89 are arranged in a southerly direction This enables precise position monitoring in each direct linear motor 81, with the aid of a position sensor 86 embodied as a magnetic field and/or hall sensor. Each direct linear motor 81 also has an integral temperature sensor 87, which allows temperature-monitored operation of the direct linear motor 81. Finally, each direct linear motor 81 comprises a micro-electronic device 90, which is connected via a connecting lead 91 to a control device, for which no further details are given, for the linear motors 80, which allows independent operation of the direct linear motors 81.

The precise arrangement and fixing of the direct linear motors 81 assigned to each axle body 21, 22, 23 is described below. Each direct linear motor 81 is assigned between at least two opposing rollers 74 and between the corresponding guide rails 76. As shown in particular by FIGS. 3 and 4, the linear motor 80, to move the carrier component 43 of the third axle body 23 in the direction of the axis of movement 53, is arranged in the x-direction 63 and the magnetic rod 82, by forming the stator 83, is securely connected to the guide component 33 of the third axle body 23, whilst the coil component 84 embodied in this case as a slider 85, is securely connected to the carriage 73. At the same time, the direct linear motor 81, is arranged inside, i.e. in the receiving space of the U-profile 70 of the carriage 73 in the area of the longer of the two edge limbs, i.e. in the area of the pair of guide rollers. In this case, this arrangement has been selected so that the central axis of the direct linear motor 81 of the third axle body 23 and the centre of gravity and/or the centroidal axis of the tri-axial handling apparatus 20 embodied by the three axle bodies 21, 22, 23 connected for functional purposes, are approximately aligned. This ensures a long-term reliable, tilt-free operation of the tri-axial handling apparatus 20.

Figure 5:
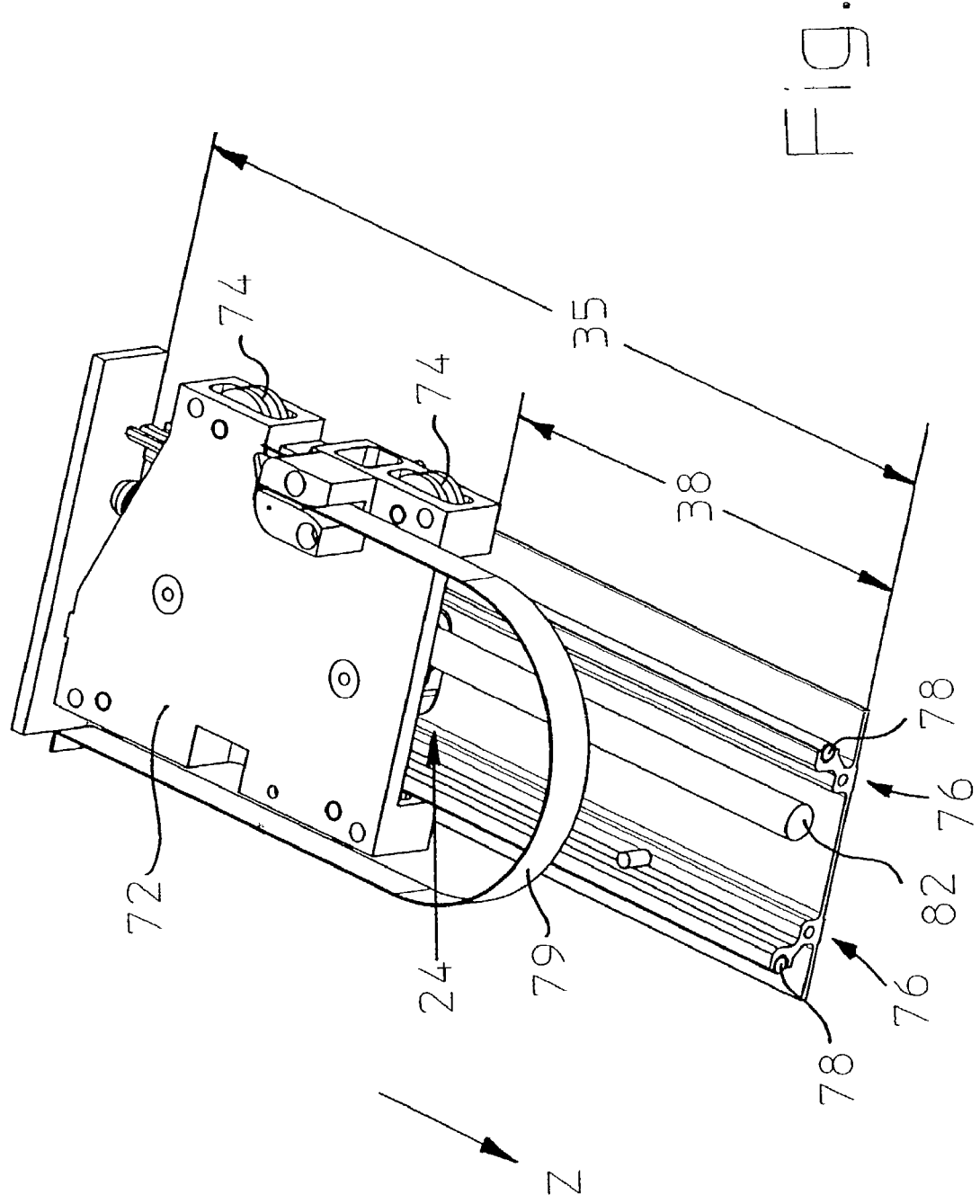
FIG. 5: a three-dimensional view of the second axle body that is assigned the vertical axis of movement.
Figure 6:
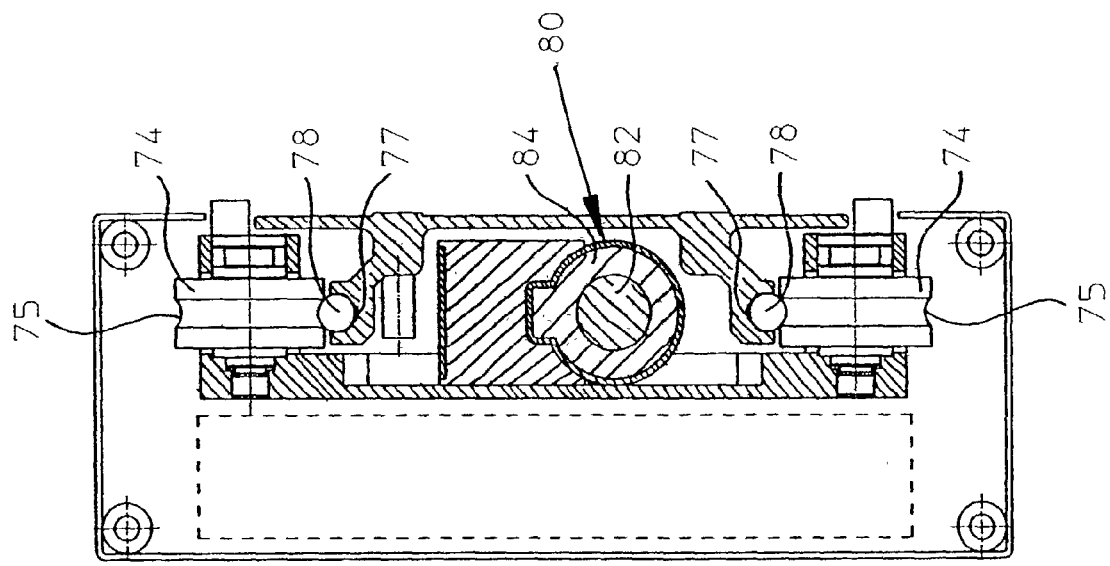
FIG. 6: a front view of the second axle body in accordance with FIG. 5, from which the front cover plate has been removed.

As shown in particular by FIGS. 5 and 6, the direct linear motor 81 assigned to the second axle body 22, i.e. the z-axis, is arranged in the receiving space formed by the profile limbs for the shafts 78 between the guide rails 76 formed by the shafts 78, wherein the central axis of which is arranged parallel to the z-direction 62 by forming the axis of movement 52. On this direct linear motor 81, the magnetic rod 82 is also formed as a stator 83, whilst the coil component 84 is embodied as a slider 85 Accordingly, the magnetic rod 82 is securely connected to the guide component 32, whilst the coil component 84 is securely connected to the carriage 72. The receiving space shown in FIG. 6 as a square with doffed lines allows the flexible and strip-shaped connection cable (79) to be received and guided and also enables a mechanism designed to compensate for the gravitational force acting on the slider 85 of the linear motor 80 movable along the travel path and a load to be carried and moved by it, in this case the micro-tier plate 45 and where applicable the fluid contained therein.

Although no further details are revealed by the Figures, the direct linear motor assigned to the first axle body 21 for moving the carriage 71 in a y-direction 61, i.e. in the direction of the axis of movement 51, is also arranged and secured such that its magnetic rod is securely connected to the guide component 31 of the first axle body 21, whilst its coil component is securely connected to the carriage 71.

The invention claimed is:

1. A tri-axial handling apparatus comprising at least three axle bodies, each exhibiting a guide component and a carrier component which by means of a drive is translationally movable on the guide component in the direction of an axis of movement, wherein at least three axes of movement respectively form a space angle to each other and are each positioned vertically to each other, wherein a guide component of a first axle body is secured to the carrier component of a second axle body, whose guide component is secured to the carrier component- of a third axle body, wherein the carrier component of the first axle body forms a handling carrier designed to enable a handling operation within a manipulation area determined by the axes of movement, wherein each said drive for the respective carrier component is a linear motor secured to the respective axle body, wherein said linear motor is embodied as an electro-magnetic direct linear motor having a magnetic rod and a coil component, and wherein at least one of the at least three axle bodies comprises a mechanism to compensate for gravitational force acting on the respective linear motor.

2. A tri-axial handling apparatus in accordance with claim 1, wherein said magnetic rod is securely connected to the guide component and that the coil component is securely connected to the movable carrier component.

3. A tri-axial handling apparatus in accordance with claim 2, wherein said magnetic rod comprises at least two permanent magnets arranged in consecutive alternating polarity.

4. A tri-axial handling apparatus in accordance with claim 1, -wherein said carrier component of said first axle body is movable on its guide component in the direction of a horizontal axis of movement, that said carrier component of said second axle body is movable on its guide component in the direction of a vertical axis of movement, and that said carrier component of said third axle body is movable on its guide component in the direction of a horizontal axis of movement.

5. A tri-axial handling apparatus in accordance with claim 1, wherein at least one carrier component and/or one guide component is embodied with a C-shaped or U-shaped profile whose profile limbs delimit a receiving space open to the outside, wherein a carrier component can be moved at least partially into the receiving space of its guide component, an adjacent guide component and/or an adjacent carrier component.

6. A tri-axial handling apparatus in accordance with claim 5, wherein said guide component of the third axle body is embodied with a profile extending in the direction of the corresponding axis of movement, said profile comprising a basic profile from which two parallel edge limbs each extend in a direction vertical to the direction of the axis of movement, wherein the guide component of the second axle body is secured to the basic profile of the guide component of the third axle body and extends at least partially between the edge limbs, yet offset from them in such a way that the carrier component guided on the second guide component can be moved at least partially within the C-shaped or U-shaped profile of the guide component of the third axle body.

7. A tri-axial handling apparatus in accordance with claim 5, wherein said carrier component guided on the third guide component is at least partially received and movable within the C-shaped or U-shaped profile of the guide component of the third axle body.

8. A tri-axial handling apparatus in accordance with claim 1, wherein the, or each, carrier component is embodied as a carriage with at least two opposing rollers provided with guide slots along their perimeter and open to the outside, which are guidingly mounted on appropriately designed guide rails of the respective guide component, wherein the guide rails extend in the direction of the respective axis of movement.

9. A tri-axial handling apparatus in accordance with claim 8, wherein said guide rails are embodied as shafts made of steel and secured in the receiving grooves of the guide component.

10. A tri-axial handling apparatus in accordance with claim 1, wherein each guide component exhibits an axial length and that a travel path is assigned to each carrier component guided on this guide component, wherein for each axle body the ratio of travel path to axial length is greater than or equal to 0.3.

11. A tri-axial handling apparatus in accordance with claim 1, wherein said guide components are formed by a process of extruding or drawing aluminium profiles.

12. A tri-axial handling apparatus in accordance with claim 1, wherein said linear motor is arranged between the at least two opposing rollers and the corresponding guide rails.

13. A tri-axial handling apparatus comprising at least three axle bodies, each exhibiting a guide component and a carrier component which by means of a drive is translationally movable on the guide component in the direction of an axis of movement, wherein at least three axes of movement respectively form a space angle to each other and are each positioned vertically to each other, wherein a guide component of a first axle body is secured to the carrier component of a second axle body, whose guide component is secured to the carrier component of a third axle body, wherein the carrier component of the first axle body forms a handling carrier designed to enable a handling operation within a manipulation area determined by the axes of movement, wherein the carrier component of at least one of the at least three axle bodies has a drive that is a linear motor, wherein said linear motor is an electro-magnetic direct linear motor having a magnetic rod and a coil component, and wherein the at least one of the at least three axle bodies comprises a mechanism to compensate for gravitational force acting on the respective axle body.

* * * * *